(12) United States Patent
Govari

(10) Patent No.: US 10,939,863 B2
(45) Date of Patent: Mar. 9, 2021

(54) DETERMINING OCCURRENCE OF FOCAL AND/OR ROTOR ARRHYTHMOGENIC ACTIVITY IN CARDIAC TISSUE REGIONS

(71) Applicant: BIOSENSE WEBSTER (ISRAEL) LTD., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 65 days.

(21) Appl. No.: 16/423,467

(22) Filed: May 28, 2019

(65) Prior Publication Data

US 2020/0375489 A1 Dec. 3, 2020

(51) Int. Cl.
| | |
|---|---|
| A61B 5/361 | (2021.01) |
| A61B 5/00 | (2006.01) |
| A61B 5/287 | (2021.01) |
| A61B 5/316 | (2021.01) |
| A61B 5/363 | (2021.01) |
| A61B 5/024 | (2006.01) |

(52) U.S. Cl.
CPC .............. *A61B 5/361* (2021.01); *A61B 5/287* (2021.01); *A61B 5/316* (2021.01); *A61B 5/363* (2021.01); *A61B 5/743* (2013.01); *A61B 5/02405* (2013.01)

(58) Field of Classification Search
CPC ... A61B 5/046; A61B 5/0464; A61B 5/04012; A61B 5/0422; A61B 5/743; A61B 5/02405
See application file for complete search history.

(56) References Cited

U.S. PATENT DOCUMENTS

| | | |
|---|---|---|
| 9,433,365 B1 | 9/2016 | Lin |
| 2003/0194057 A1 | 10/2003 | Dewaele |
| 2004/0010188 A1 | 1/2004 | Wasserman |
| 2006/0084970 A1 | 4/2006 | Beatty et al. |
| 2006/0116576 A1* | 6/2006 | McGee ................ A61B 8/0833 600/434 |
| 2009/0048528 A1 | 2/2009 | Hopenfeld et al. |
| 2013/0079653 A1 | 3/2013 | Shim et al. |

(Continued)

FOREIGN PATENT DOCUMENTS

WO WO2017165846 A1 9/2017

OTHER PUBLICATIONS

U.S. Appl. No. 16/289,843, filed Mar. 1, 2019.
European Search Report for corresponding EPA No. 20176837.1 dated Oct. 8, 2020.

*Primary Examiner* — Gary Jackson
*Assistant Examiner* — Sebastian X Lukjan

(57) ABSTRACT

A method includes receiving, in a processor, a two-dimensional (2D) electroanatomical (EA) map of an interior surface of at least a portion of a cavity of an organ of a patient, the 2D EA map including electrophysiological (EP) values measured at respective locations on the interior surface. A complex analytic function is fitted to a set of the EP values that were measured in a given region of the 2D EA map. A singularity is identified in the fitted complex analytic function. The region is projected onto a three-dimensional (3D) EA map of the interior surface. At least part of the 3D E A map is presented to a user, including indicating an arrhythmogenic EP activity at a location on the 3D E A map corresponding to the singularity identified in the fitted complex analytic function.

18 Claims, 4 Drawing Sheets

(56) References Cited

U.S. PATENT DOCUMENTS

| | | | |
|---|---|---|---|
| 2014/0278129 A1* | 9/2014 | Voth | A61B 5/0402 |
| | | | 702/19 |
| 2015/0230721 A1 | 8/2015 | Lo | |
| 2016/0354142 A1* | 12/2016 | Pearson | A61B 34/10 |
| 2017/0055864 A1* | 3/2017 | Han | A61B 5/743 |
| 2018/0325400 A1 | 11/2018 | Dubois | |

* cited by examiner

DETERMINING OCCURRENCE OF FOCAL AND/OR ROTOR ARRHYTHMOGENIC ACTIVITY IN CARDIAC TISSUE REGIONS

FIELD OF THE INVENTION

The present invention relates generally to cardiac mapping, and particularly to analyzing anatomical cardiac maps.

BACKGROUND OF THE INVENTION

Attempts to model cardiac electrophysiological activity were previously reported in the patent literature. For example, U.S. Patent Application Publication 2013/0079653 describes an arrhythmia-diagnosing method and device for diagnosing arrhythmias, such as fibrillation or tachycardia. The arrhythmia-diagnosing method includes the following steps: measuring (a) the heart characteristic length, and the (b) frequency and (c) conduction velocity of the cardiac electrical wave; and (d) determining the occurrence or absence of an arrhythmia by using a non-dimensional number obtained by processing the three parameters measured in steps (a) to (c). With the non-dimensional parameter, it is possible to predict and diagnose an electrical wave tornado, one of the causes of arrhythmia. To analyze the electrical wave conduction occurring in cardiac tissues and derive the non-dimensional parameter, a voltage wave diffusion equation is converted into a non-dimensional equation.

As another example, U.S. Patent Application Publication 2006/0084970 describes a method of mapping electrophysiological data in a heart chamber. The acquired electrophysiological data is integrated with determined respective location data. An algorithm is disclosed, that employs electrostatic volume-conductor field theory to assist in deriving a high-resolution electrophysiological map of the chamber volume.

SUMMARY OF THE INVENTION

An embodiment of the present invention provides a method, including receiving, in a processor, a two-dimensional (2D) electroanatomical (EA) map of an interior surface of at least a portion of a cavity of an organ of a patient, the 2D EA map including electrophysiological (EP) values measured at respective locations on the interior surface. A complex analytic function is fitted to a set of the EP values that were measured in a given region of the 2D EA map. A singularity is identified in the fitted complex analytic function. The region is projected onto a three-dimensional (3D) EA map of the interior surface. At least part of the 3D EA map is presented to a user, including indicating an arrhythmogenic EP activity at a location on the 3D EA map corresponding to the singularity identified in the fitted complex analytic function.

In some embodiments, identifying the singularity includes identifying a focal singularity, and indicating the arrhythmogenic EP activity includes indicating a focal arrhythmogenic EP activity.

In some embodiments, identifying the singularity includes identifying a rotor singularity, and indicating the arrhythmogenic EP activity includes indicating a rotor arrhythmogenic EP activity.

In an embodiment, identifying the singularity and presenting the arrhythmogenic EP activity includes distinguishing between a focal arrhythmogenic EP activity and a rotor arrhythmogenic EP activity.

In another embodiment, receiving the 2D map EA map includes receiving a 2D EA map projected from a respective 3D EP map using a predefined coordinate transformation.

In some embodiments, the measured EP values include local activation time (LAT) values. In other embodiments, the measured EP values include voltages.

In some embodiments, identifying the singularity includes calculating one or more residues of the complex analytic function in the given region.

In some embodiments, the one or more residues are indicative of one or more focal sources.

In an embodiment, identifying the singularity includes calculating one or more residues of a directional derivative of the complex analytic function along a curve encircling the given region. In another embodiment, the one or more residues are indicative of one or more rotor circuits.

There is additionally provided, in accordance with an embodiment of the present invention, a system, including a memory and a processor. The memory is configured to store a two-dimensional (2D) electroanatomical (EA) map of an interior surface of at least a portion of a cavity of an organ of a patient, the 2D EA map including electrophysiological (EP) values measured at respective locations on the interior surface. The processor is configured to (a) fit a complex analytic function to a set of EP values that were measured in a given region of the 2D EA map, (b) identify a singularity in the fitted complex analytic function, (c) project the region onto a three-dimensional (3D) EA map of the interior surface, and (d) present at least part of the 3D EA map to a user, including indicating an arrhythmogenic EP activity at a location on the 3D EA map corresponding to the singularity identified in the fitted complex analytic function.

The present invention will be more fully understood from the following detailed description of the embodiments thereof, taken together with the drawings in which:

DETAILED DESCRIPTION OF EMBODIMENTS

Overview

Figure 1:
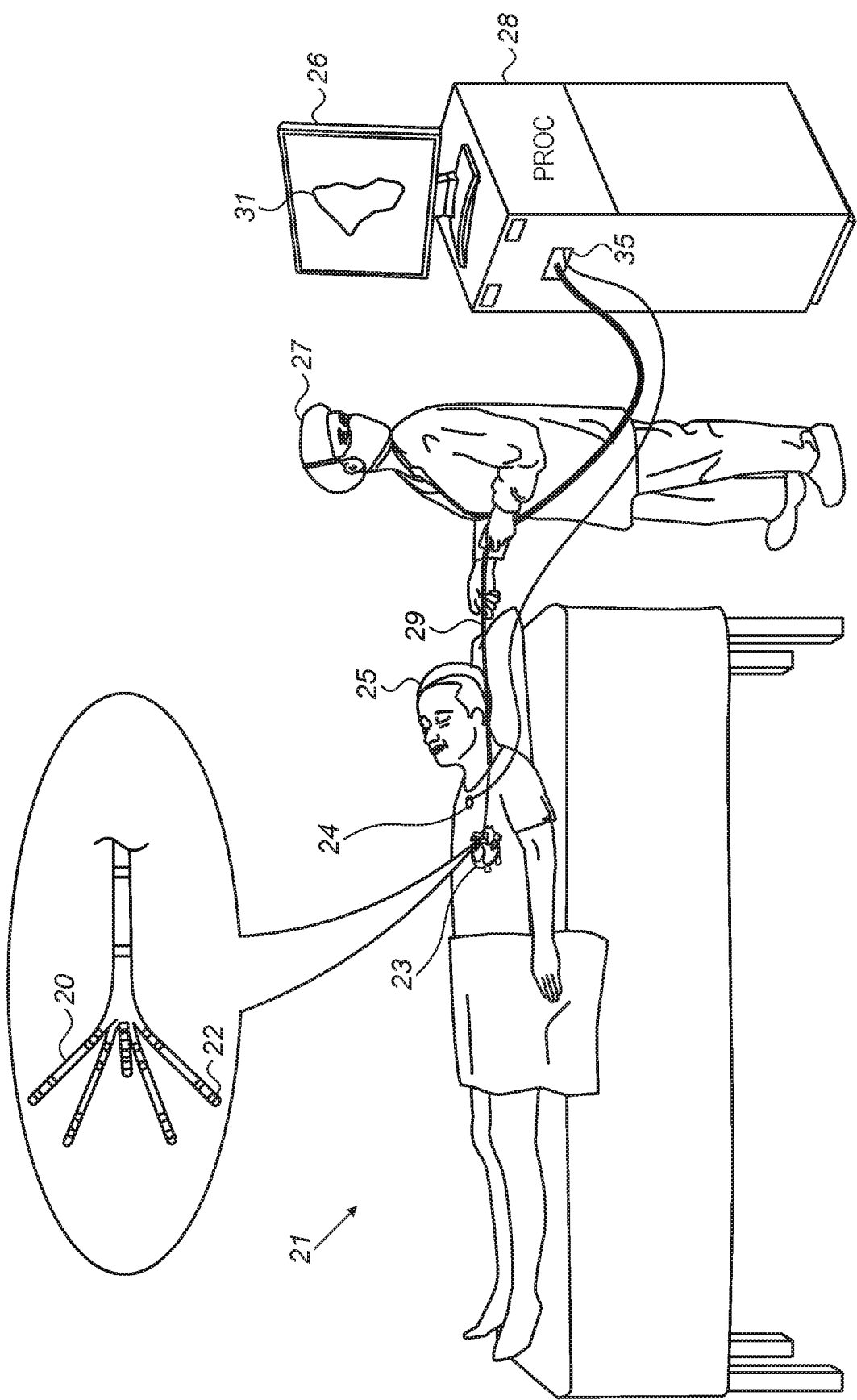
FIG. 1 is a schematic, pictorial illustration of a system for electroanatomical (EA) mapping, in accordance with an embodiment of the present invention.

Catheter-based electroanatomical mapping techniques may produce various types of electroanatomical (EA) maps of an inner surface of a cavity of an organ, such as a left atrium of a heart. Typically, an EA map provides a distribution of an electrophysiological (EP) parameter overlaid on a rendered three-dimension (3D) anatomy. Examples of EP overlaid parameters include voltages (i.e., potentials) and activation times. A user, such as a physician, may attempt to interpret a 3D EA map to determine if a given distribution of EP values over the 3D rendered anatomy is indicative of aberrant EP activity, and to identify tissue locations on the inner surface that cause the aberrant EP activity.

Typically, aberrant cardiac EP activity is either a focal type of arrhythmogenic activity or a spiral (i.e., rotor) type of arrhythmogenic activity. In focal arrhythmia, the EP potential largely flows in a radial direction away from a focal source. In rotor arrhythmia the EP potential largely flows in an azimuthal direction about a center of rotation.

Analysis of a surface of a 3D EA map, i.e., of a manifold embedded in 3D space, is very difficult, and requires significant algorithmic and computational power. Furthermore, such an analysis might be incomplete, for example because full analysis of a manifold in 3D space requires more information than is available from the measured EP values.

Attempting to model EP activity on a 3D EA embedded manifold typically results is a description of a flow of a respective EP parameter (e.g., bioelectric potential) as a solution of an equation of wave propagation. Examples of such equations include variants of wave equations and of wave diffusion equations, and therefore modeling the EP activity would attempt to calculate explicit time-dependent EP wave propagating solutions. Unfortunately, the complex behavior of EP signal flow in cardiac tissue makes it difficult to conclude which of the different possible model equations best reflects reality.

Embodiments of the present invention that are described hereinafter provide improved methods and systems for identifying an occurrence of focal and/or rotor arrhythmogenic activity in given regions of cardiac tissue. The disclosed technique analyzes the EP activity on a 2D EA map projected from the 3D EA map onto a complex 2D plane $\mathbb{C}$, by applying methods of complex analysis to the projected 2D EA map, and in this manner obtains the indications of the types of arrhythmia and their locations.

In particular, to obtain a complex analytic (i.e., holomorphic) solution in $\mathbb{C}$, to be analyzed over a given region of the projected 2D EA map, the disclosed technique uses a 2D version of a 3D Laplacian term that the above equations for 3D wave propagation include. For that, the method fits each set of measured EP values in a given region of the 2D EA projected map with a unique harmonic solution of the 2D Laplacian term over that region, and extends the harmonic solution into a holomorphic one, as described below.

The disclosed methods thus greatly simplify the analysis by (a) reducing the Laplacian term from 3D to 2D by projecting the EP manifold from 3D to 2D, (b) fitting the data with a complex analytic function solution of a respective 2D Poisson equation (i.e., generalized Laplace equation) and (c) analyzing the fitted 2D holomorphic solution to identify occurrence of focal and/or rotor arrhythmogenic activity.

Among the numerous possible solutions of a 2D Poisson equation of the disclosed methods for each given 2D region of the 2D EP map, is one that provides a unique complex analytic solution that fits a measured set of EP values in the given region. This unique solution is indicative of the EP activity in the region, being either free stream (e.g., normal) propagation of EP potentials, or being at least one resulting of one or more focal sources and/or one or more rotor circuits in located in the 2D region.

Though the EP activity is time-dependent, an arrhythmia is sufficiently determined by analyzing a measured distribution of EP values at a given instance, using the fitted analytic function as described below.

In some embodiments, a processor receives a 2D EA map that is projected from a respective three-dimensional (3D) EP map of an interior surface of at least a portion of a cavity of an organ of a patient, using a predefined coordinate transformation. The parameters of the predefined transformation can be subsequently used by the processor to back-project the analyzed 2D EA map into a 3D EA map. In other embodiments, the processor itself projects a 3D EP map onto a 2D plane to generate the projected 2D EA map.

Either way, the 2D EA map is overlaid with EP values, such as potential values or local activation time (LAT) values, which are measured at respective projected locations on the 3D EA map. Then, at any given region of the 2D EA map, a processor fits a complex analytic function to the measured EP values in the region. The processor analyzes the fitted function to determine whether one or more focal-singularity and rotor-singularity types of arrhythmogenic EP activity exist in the given region. The processor analyzes a sufficient number of regions to cover the required portion of the organ. Then, the processor projects the indicated 2D regions back onto the 3D EA map to indicate one or more respective regions in which arrhythmogenic EP activity occurs, as well as its type. Finally, the processor presents the region indicative 3D EA map to a user.

In some embodiments, the processor determines whether a given region on the 2D EA map hosts one or more focal sources by estimating the number of residues of a complex analytic function fitted to the EP data in that region. The residues are calculated by a line integration of the complex analytic function over a curve encircling the region. Similarly, the processor determines whether the given region hosts one or more locations of rotor flow based on estimating the number of residues of a directional derivative of the same complex analytic function.

If integration over both the complex analytic function and its directional derivative yield zero value, then the processor concludes that the given region is free of locations demonstrating focal or rotor types of arrhythmogenic EP activity. If integration over the complex analytic function yields a finite number of residues while integration over its directional derivative integration yields a zero value, then the processor deduces that the given region includes one or more locations demonstrating focal arrhythmogenic EP activity. If integration over the complex analytic function yields zero value while integration over its directional derivative yields a finite number of residues, then the processor deduces that the given region includes one or more locations demonstrating rotor arrhythmogenic EP activity.

Typically, the processor is programmed in software containing a particular algorithm that enables the processor to conduct each of the processor related steps and functions outlined above.

The disclosed technique may simplify the interpretation of EA maps and reduce requirements from computation resources, and by doing so provide more accurate and accessible catheter-based cardiac diagnosis.

System Description

FIG. 1 is a schematic, pictorial illustration of a system for electroanatomical (EA) mapping, in accordance with an embodiment of the present invention. FIG. 1 depicts a physician 27 using an EA Pentaray® catheter 29 to perform an EA mapping of a heart 23 of a patient 25. Catheter 29 comprises, at its distal end, one or more arms 20, which may be mechanically flexible, each of which is coupled with one or more electrodes 22. During the mapping procedure, electrodes 22 acquire and/or inject unipolar and/or bipolar signals from and/or to the tissue of heart 23. A processor 28 receives these signals via an electrical interface 35, and uses information contained in these signals to construct a 3D EA map 31. During and/or following the procedure, processor 28 may display EA map 31 on a display 26. In some embodiments, EA map 31 comprises measured LAT values, as shown in FIG. 2.

During the procedure, a tracking system is used to track the respective locations of sensing electrodes 22, such that each of the signals may be associated with the location at which the signal was acquired. For example, the Active Current Location (ACL) system, made by Biosense-Webster (Irvine Calif.), which is described in U.S. Pat. No. 8,456,182, whose disclosure is incorporated herein by reference, may be used. In the ACL system, a processor estimates the respective locations of the electrodes based on impedances measured between each of the sensing electrodes 22, and a plurality of surface electrodes 24, that are coupled to the skin of patient 25. For example, three surface electrodes 24 may be coupled to the patient's chest, and another three surface electrodes may be coupled to the patient's back. (For ease of illustration, only one surface electrode is shown in FIG. 1.) Electric currents are passed between electrodes 22 inside heart 23 of the patient and surface electrodes 24. Processor 28 calculates an estimated location of all electrodes 22 within the patient's heart based on the ratios between the resulting current amplitudes measured at surface-electrodes (or between the impedances implied by these amplitudes) and the known positions of electrodes 24 on the patient's body. The processor may thus associate any given impedance signal received from electrodes 22 with the location at which the signal was acquired.

The example illustration shown in FIG. 1 is chosen purely for the sake of conceptual clarity. Other tracking methods can be used, such as ones based on measuring voltage signals, as with the Carto®4 system (produced by Biosense Webster). Other types of sensing catheters, such as the Lasso® Catheter (produced by Biosense Webster) may equivalently be employed. Contact sensors may be fitted at the distal end of EA catheter 29. As noted above, other types of electrodes, such as those used for ablation, may be utilized in a similar way, fitted to electrodes 22 for acquiring the needed position data. Thus, an ablation electrode used for collecting position data is regarded, in this case, as a sensing electrode. In an optional embodiment, processor 28 is further configured to indicate the quality of physical contact between each of the electrodes and an inner surface of the cardiac chamber during measurement.

Processor 28 typically comprises a general-purpose computer with software programmed to carry out the functions described herein. In particular, processor 28 runs a dedicated algorithm as disclosed herein, including in FIG. 4, that enables processor 28 to perform the disclosed steps, as further described below. The software may be downloaded to the computer in electronic form, over a network, for example, or it may, alternatively or additionally, be provided and/or stored on non-transitory tangible media, such as magnetic, optical, or electronic memory.

Figure 2A:
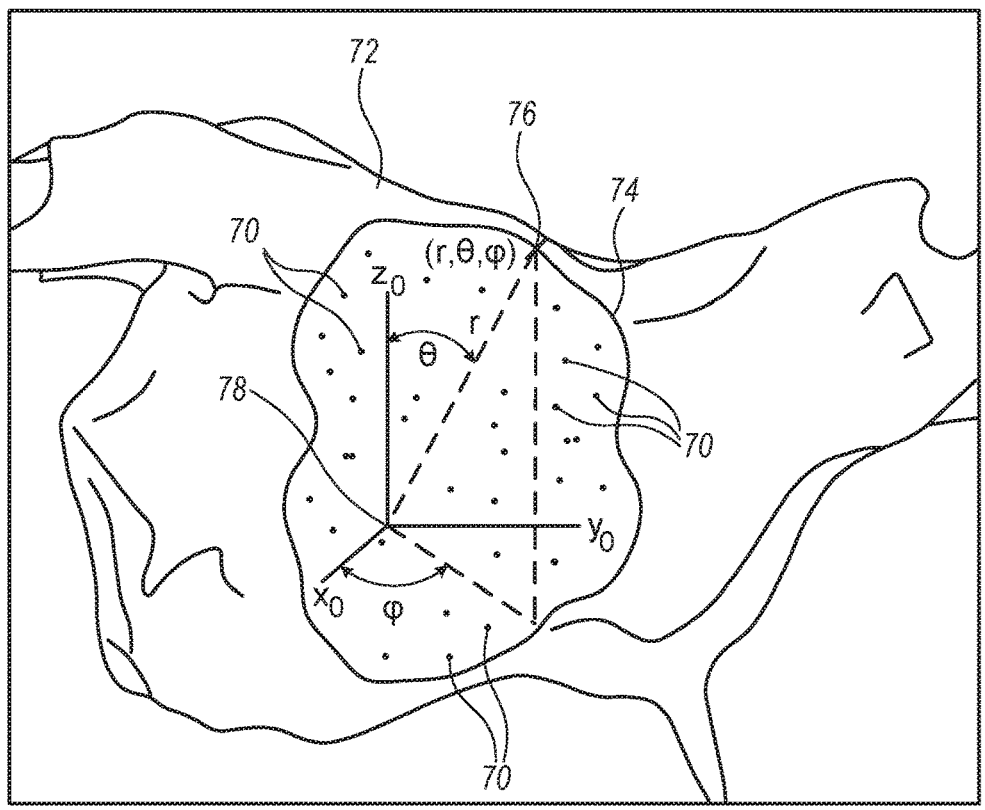
FIGS. 2A and 2B show a cutaway view of a 3D electroanatomical (EA) map of an interior surface of a cavity received by the system of FIG. 1, and a plan view of a projected 2D EA map, respectively, in accordance with an embodiment of the present invention.
Figure 2B:
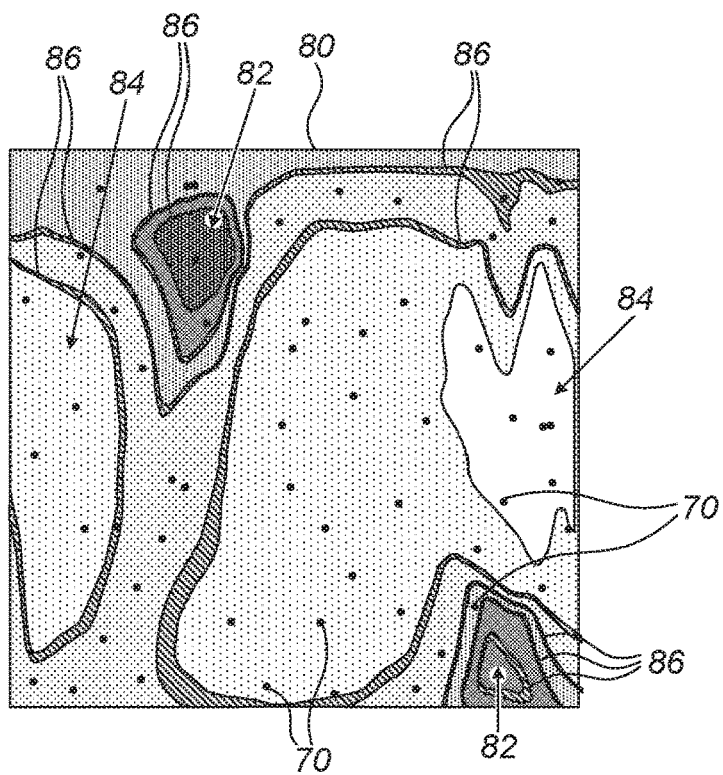

Determining Occurrence of Focal and/or Rotor Arrhythmogenic Activity in Cardiac Tissue Regions FIGS. 2A and 2B show a cutaway view of a 3D electro-anatomical (EA) map 72 of interior surface of a cavity received by the system of FIG. 1, and a plan view of a projected 2D EA map 80, respectively, in accordance with an embodiment of the present invention. 3D EA map 72 comprises EP values 70, such as potentials, measured at respective locations 76 on the inner surface. Locations 76 are defined in a 3D coordinate system (shown by both orthogonal and spherical coordinates) having an origin 78. A section 74 has been cut away from the interior surface in order to show how locations 76 (only one shown for the sake of simplicity) are defined.

FIG. 2B shows 2D EP map 80 in which the surface topography was encoded by processor 28 using contour lines 86 and patterns, such that a user viewing the map can perceive relative elevations of the projected topography. The encoded 2D EA map includes depressions 82 and elevations 84. As seen, 2D EA map 80 retains EP values 70 that processor 28 overlaid at respective projected locations on the 2D map.

A projection to and from the 3D map and a partially flattened 2D map is typically performed according to any suitable coordinate transformation. A method for performing the projections between the maps shown in FIGS. 2A and 2B in is described in U.S. patent application Ser. No. 16/289,843, filed Mar. 1, 2019, entitled "Map of Body Cavity," which is assigned to the assignee of the present patent application and whose disclosure is incorporated herein by reference.

In some embodiments, processor 28 performs the analysis of EP flow on a strictly flat 2D EP map, which simplifies the calculation, relative, for example to using non-flat 2D manifolds. In general, however, the calculations, e.g., line integrals, can be performed on non-flat surfaces.

In an embodiment, the calculations performed herein by processor 28 use a 2D coordinate system, whereas relative elevation values, which are locally mostly small, are ignored (e.g., approximated to be zero). Alternatively, to maintain simplified strict 2D conditions without an approximation, regions in question on the 2D EA map may be defined only within an area encoded as having the same elevation, such as shown by way of example in FIG. 3.

Figure 3C:
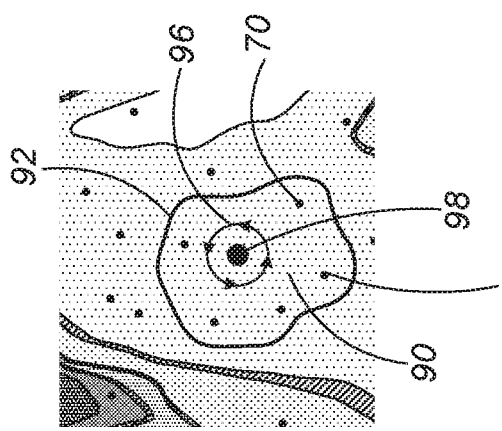
FIGS. 3A-3C are partial plan views of the projected 2D electroanatomical (EA) map of FIG. 2, showing normal, focal, and rotor EP potential flows, respectively, in accordance with embodiments of the present invention.
Figure 3B:
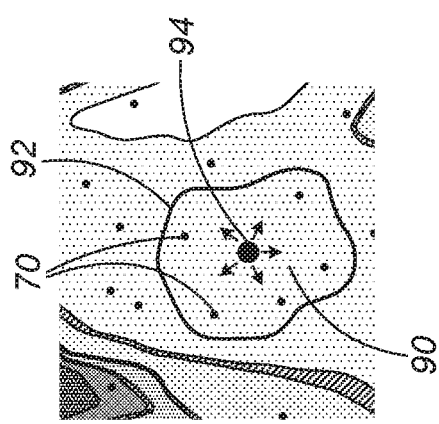
Figure 3A:
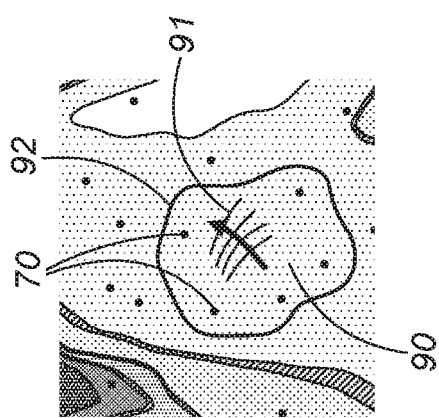

FIGS. 3A-3C are partial plan views of the projected 2D electroanatomical (EA) map of FIG. 2, showing normal, focal, and rotor EP potential flows, respectively, in accordance with embodiments of the present invention. Either normal or aberrant EP activity can be indicated using a complex analytic function $\varphi(z)$, with $z=re^{i\theta}$ where $(r,\theta)$ being polar coordinates, constructed using a solution $u(r,\theta)$ of a 2D Poisson equation describing a distribution of, for example, an EP potential function.

In the present context, a complex function $\varphi(z)$ is defined as an analytic function in a given region of the complex plane $\mathbb{C}$ if $\varphi(z)$ is differentiable at any point of that region, with the possible exception of isolated points in the region in which $\varphi(z)$ is singular (e.g., has a pole). Typically, a complex analytic function is infinitely differentiable in the given region of the complex plane (other than isolated singularities). Put in another way, the Taylor series of a complex analytic function converges to the value of the function for any point in the given region of the complex plane (other than isolated singularities).

The function $\varphi(z)$ can be written as $\varphi(r,\theta)=u(r,\theta)+iv(r,\theta)$, where $u(r,\theta)$ and $v(r,\theta)$ are real functions and and $v(r,\theta)$ is related to $u(r,\theta)$ via the Cauchy-Riemann equations, $$\frac{\partial u}{\partial r} = \frac{1}{r}\frac{\partial v}{\partial \theta} \text{ and } \frac{\partial v}{\partial r} = -\frac{1}{r}\frac{\partial u}{\partial \theta}.$$

$u(r,\theta)$ is a sum of a harmonic solution of the Laplace equation and a particular solution, and therefore function $u(r,\theta)$ is a solution of the Poisson equation:

$$\frac{\partial^2 u}{\partial r^2} + \frac{1}{r}\frac{\partial u}{\partial r} + \frac{1}{r^2}\frac{\partial^2 u}{\partial \theta^2} = S(r,\theta) \qquad \text{Eq. 1}$$

In Eq. 1, if the source term $S(r,\theta)$ is non-zero than a unique EP potential function $u(r,\theta)$ that solves Eq. 1 describes potentials resulting from a focal source. Otherwise, Eq. 1 is homogenous, and $u(r,\theta)$ may describes free stream (e.g., normal) or vortex types of EP potential distributions which a respective normal flow or vortex flow underlines (91 in FIG. 3A).

A solution $u(r,\theta)$ for Eq. 1 can be spanned, for example, by a linear combination of base functions of any chosen basis. However, a basis of Bessel functions and associated Legendre polynomials is of particular usefulness due to the focal/rotor geometry of the aberrant activity. In such a case the analytic solution $u(r,\theta)$ can be approximated by:

$$u(r,\theta) \cong \Sigma_{nl}(a_n l r^{-l-1} + b_n r^l) P_l(\cos\theta) \qquad \text{Eq. 2}$$

In Eq. 2, the potential function $u(r,\theta)$ solution is a linear combination of several base functions (i.e., with indices n and l being limited to several values) and serves as a good approximation to an exact holomorphic function over a limited size region of 2D EA map 80 that reflects the EP potential measured by EP values 70 at that region. The optimal size of the region depends on the number of data points in the region.

The explicit form of $u(r,\theta)$ is derived by substituting measured EP values 70 into Eq. 2 at respective locations $r_j,\theta_j$ inside the given region and solving an inhomogeneous linear system of equations to extract $a_n$ and $b_n$. The accuracy of the fitted function $u(r,\theta)$ depends on the number of available EP values at the region, as the number of solvable $a_n$ and $b_n$ coefficients in Eq. 2 equals the number of measured data points at the given region.

With $u(r,\theta)$ derived, holomorphic (i.e., complex analytic) function $\varphi(z)$ can be constructed, using the properties of $f(z)$ described above.

Some embodiments of the present invention indicate whether one or more focal-singularities or rotor-singularities exist in a given region (e.g., region 90) of the 2D EA map by calculating line integral $\oint \varphi(z)d\gamma$ over a curve $\gamma$ (e.g., curve 92) encircling the given region of function $\varphi(z)$ and of a directional derivative of the complex analytic flow function $\nabla_\gamma \varphi(z) \cdot \hat{\gamma}$ calculated also along the curve $\gamma, \oint \nabla_\gamma \varphi(z) \cdot \hat{\gamma} d\gamma$.

According to the residue theorem, if the two above line integrals both equal zero, the corresponding EP values to which $u(r,\theta)$ was fitted describe a free stream normal flow (e.g., in flow 92 in FIG. 2A) in the given region.

When the line integral of the function $\varphi(z)$ is non-zero and that of $\nabla_\gamma \varphi(z)$ equals zero, the corresponding EP values to which $\varphi(z)$ was fitted describe EP flow due to a focal source at the given region, i.e., describe focal arrhythmogenic source in the given region (e.g., focal source 94 in FIG. 2B).

When the line integral of the function $\varphi(z)$ is zero and that of $\nabla_\gamma \varphi(z)$ is non-zero, the corresponding EP values to which $\varphi(z)$ was fitted describe irrotational vortex EP flow (e.g., vortex 96) at the given region, i.e., describe a rotor arrhythmogenic circuit in the given region (e.g., rotor circuit 98 in FIG. 2C).

It may be possible that a few arrhythmogenic locations exist in a given region. Each of the above line integrals, when non-zero, then gives a result in the form $2\pi i \Sigma_{k=1}^N \text{Res}(\varphi,\xi_k)$, or $2\pi i \Sigma_{k=1}^M \text{Res}(\nabla_\gamma \varphi,\eta_k)$. N and M are the integer numbers of arrhythmogenic locations of the specific type (i.e., focal or rotor) of arrythmia yielding. Each location yields residue values $\xi_k$ and $\eta_k$ of the respective analytic functions $\varphi$ and $\nabla_\gamma \varphi$. Therefore, the disclosed method is capable of indicating the existence of multiple arrhythmogenic locations in a small region.

Figure 4:
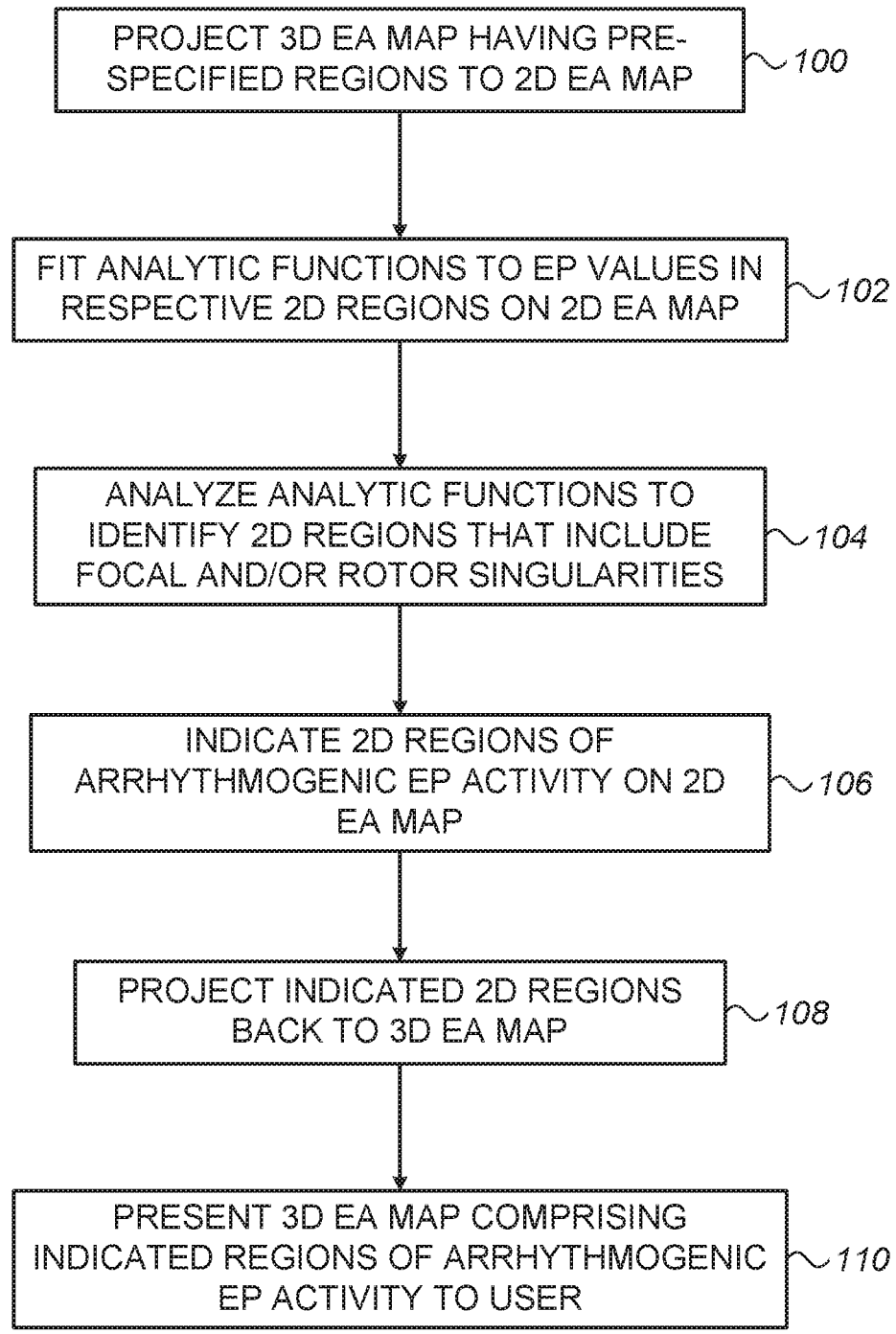
FIG. 4 is a flow chart that schematically describes a method for determining occurrence of focal and/or rotor arrhythmogenic activity in cardiac tissue regions of the 3D EA map of FIG. 2, in accordance with an embodiment of the present invention.

FIG. 4 is a flow chart that schematically describes a method for determining the occurrence of focal and/or rotor arrhythmogenic activity in cardiac tissue regions of the 3D EA map of FIG. 2, in accordance with an embodiment of the present invention. The algorithm according to the presented embodiment carries out a process that begins with processor 28 projecting onto a 2D plane, using a predefined coordinate transformation, a 3D EP map 72 having prespecified regions, to create a 2D EA map, at an EP map projection step 100. By way of example, 2D region 90 of the projected EP map is a respective region to a prespecified region on 3D EP map 72. Typically, the 2D EA map is overlaid with EP values, such as potential values or local activation time (LAT) values, that were measured at respective projected locations on the 3D EA map.

Next, processor 28 fits complex analytic functions to measured EP values at the respective 2D regions of the 2D EA map, using the process described above, at a fitting step 102.

Next, processor 28 analyzes each analytic function by solving line integrals, as described above, to indicate whether at least one, or more, focal-singularities and rotor-singularities types of arrhythmogenic EP activity exist in any of the 2D regions (i.e., to identify arrhythmogenic regions), at an arrhythmia analysis step 104.

Processor 28 then indicates (e.g., tags) regions on the 2D EP map in which arrhythmogenic activity occurs, at region indication step 106. This step typically includes an indication of arrhythmia type.

Next, the processor projects the indicated 2D regions back onto the 3D EA map which maintains an indication of number and type of arrhythmogenic sites per region, at regions back-projection step 108.

Finally, the processor presents the region indicative 3D EA map to a user, at a map presenting step 110.

The example flow chart shown in FIG. 4 is chosen purely for the sake of conceptual clarity. In optional embodiments, various additional steps of the algorithm may be performed, which have been omitted from the disclosure herein purposely in order to provide a more simplified flow chart. For example, a step that automatically registers additional layers with the EP maps, such as of medical images and of other parameters (e.g., tissue wall thickness to assist adjusting parameters of a subsequent ablation treatment).

Although the embodiments described herein mainly address cardiac applications, the methods and systems described herein can also be used in other applications, such as in neurology.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:

receiving, in a processor, a two-dimensional (2D) electroanatomical (EA) map of an interior surface of at least a portion of a cavity of an organ of a patient, the 2D EA map comprising electrophysiological (EP) values measured at respective locations on the interior surface;

fitting a complex analytic function to a set of the EP values that were measured in a given region of the 2D EA map;

identifying a singularity in the fitted complex analytic function, wherein identifying the singularity comprises calculating one or more residues of the complex analytic function in the given region;

projecting the region onto a three-dimensional (3D) EA map of the interior surface; and presenting at least part of the 3D EA map to a user, including indicating an arrhythmogenic EP activity at a location on the 3D EA map corresponding to the singularity identified in the fitted complex analytic function.

2. The method according to claim 1, wherein identifying the singularity comprises identifying a focal singularity, and wherein indicating the arrhythmogenic EP activity comprises indicating a focal arrhythmogenic EP activity.

3. The method according to claim 1, wherein identifying the singularity comprises identifying a rotor singularity, and wherein indicating the arrhythmogenic EP activity comprises indicating a rotor arrhythmogenic EP activity.

4. The method according to claim 1, wherein identifying the singularity and presenting the arrhythmogenic EP activity comprise distinguishing between a focal arrhythmogenic EP activity and a rotor arrhythmogenic EP activity.

5. The method according to claim 1, wherein receiving the 2D map EA map comprises receiving a 2D EA map projected from a respective 3D EP map using a predefined coordinate transformation.

6. The method according to claim 1, wherein the measured EP values comprise local activation time (LAT) values.

7. The method according to claim 1, wherein the measured EP values comprise voltages.

8. The method according to claim 1, wherein the one or more residues are indicative of one or more focal sources.

9. A system, comprising:

a memory, configured to store a two-dimensional (2D) electroanatomical (EA) map of an interior surface of at least a portion of a cavity of an organ of a patient, the 2D EA map comprising electrophysiological (EP) values measured at respective locations on the interior surface; and a processor, configured to:

fit a complex analytic function to a set of EP values that were measured in a given region of the 2D EA map;

identify a singularity in the fitted complex analytic function, wherein the processor is configured to identify the singularity by calculating one or more residues of the complex analytic function in the given region;

project the region onto a three-dimensional (3D) EA map of the interior surface; and present at least part of the 3D EA map to a user, including indicating an arrhythmogenic EP activity at a location on the 3D EA map corresponding to the singularity identified in the fitted complex analytic function.

10. The system according to claim 9, wherein the processor is configured to identify the singularity by identifying a focal singularity, and to indicate a focal arrhythmogenic EP activity to the user.

11. The system according to claim 9, wherein the processor is configured to identify the singularity by identifying a rotor singularity, and to indicate a rotor arrhythmogenic EP activity to the user.

12. The system according to claim 9, wherein the processor is configured to identify the singularity and present the arrhythmogenic EP activity by distinguishing between a focal arrhythmogenic EP activity and a rotor arrhythmogenic EP activity.

13. The system according to claim 9, wherein the processor is further configured to project the 3D EP map into a respective 2D map EA map using a predefined coordinate transformation.

14. The system according to claim 9, wherein the one or more residues are indicative of one or more focal sources.

15. A method, comprising:

receiving, in a processor, a two-dimensional (2D) electroanatomical (EA) map of an interior surface of at least a portion of a cavity of an organ of a patient, the 2D EA map comprising electrophysiological (EP) values measured at respective locations on the interior surface;

fitting a complex analytic function to a set of the EP values that were measured in a given region of the 2D EA map;

identifying a singularity in the fitted complex analytic function, wherein identifying the singularity comprises calculating one or more residues of a directional derivative of the complex analytic function along a curve encircling the given region;

projecting the region onto a three-dimensional (3D) EA map of the interior surface; and presenting at least part of the 3D EA map to a user, including indicating an arrhythmogenic EP activity at a location on the 3D EA map corresponding to the singularity identified in the fitted complex analytic function.

16. The method according to claim 15, wherein the one or more residues are indicative of one or more rotor circuits.

17. A system, comprising:

a memory, configured to store a two-dimensional (2D) electroanatomical (EA) map of an interior surface of at least a portion of a cavity of an organ of a patient, the 2D EA map comprising electrophysiological (EP) values measured at respective locations on the interior surface; and a processor, configured to:

fit a complex analytic function to a set of EP values that were measured in a given region of the 2D EA map;

identify a singularity in the fitted complex analytic function, wherein the processor is configured to identify the singularity by calculating one or more residues of a directional derivative of the complex analytic function along a curve encircling the given region;

project the region onto a three-dimensional (3D) EA map of the interior surface; and present at least part of the 3D EA map to a user, including indicating an arrhythmogenic EP activity at a location on the 3D EA map corresponding to the singularity identified in the fitted complex analytic function.

18. The system according to claim 17, wherein the one or more residues are indicative of one or more rotor circuits.

\* \* \* \* \*